(12) United States Patent
Lastovich et al.

(10) Patent No.: US 7,422,567 B2
(45) Date of Patent: Sep. 9, 2008

(54) MICROABRADER WITH CONTROLLED ABRASION FEATURES

(75) Inventors: Alexander G. Lastovich, Raleigh, NC (US); Frank E. Martin, Durham, NC (US); M. Ishaq Haider, Morrisville, NC (US); Richard P. Clarke, Raleigh, NC (US); Jason B. Alarcon, Durham, NC (US); John A. Mikszta, Durham, NC (US); John P. Dekker, III, Cary, NC (US); Weston Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 463 days.

(21) Appl. No.: 10/649,395

(22) Filed: Aug. 27, 2003

(65) Prior Publication Data

US 2004/0064087 A1 Apr. 1, 2004

Related U.S. Application Data

(60) Provisional application No. 60/406,694, filed on Aug. 29, 2002.

(51) Int. Cl.
*A61B 17/20* (2006.01)
(52) U.S. Cl. ....................................................... 604/46
(58) Field of Classification Search ............. 604/46–48; 606/167–173, 180
See application file for complete search history.

(56) References Cited

U.S. PATENT DOCUMENTS

| | | | | |
|---|---|---|---|---|
| 2,542,828 | A | * | 2/1951 | Morrison ...................... 606/85 |
| 2,688,970 | A | * | 9/1954 | Guye .......................... 604/46 |
| 3,756,242 | A | | 9/1973 | Coss |
| 3,964,482 | A | | 6/1976 | Gerstel et al. |
| 5,003,987 | A | | 4/1991 | Grinwald et al. |
| 5,250,023 | A | | 10/1993 | Lee et al. |
| 5,611,806 | A | | 3/1997 | Jang |
| 5,618,295 | A | * | 4/1997 | Min ........................... 606/171 |
| 5,679,647 | A | | 10/1997 | Carson |

(Continued)

FOREIGN PATENT DOCUMENTS

EP 0381410 8/1990

(Continued)

*Primary Examiner*—Nicholas D. Lucchesi
*Assistant Examiner*—Theodore J Stigell
(74) *Attorney, Agent, or Firm*—Robert E. West (57) ABSTRACT

An abrader device for delivering a substance into skin via an abrasion process includes a housing adapted to be pressed against the skin at a desired delivery site, an applicator head disposed in an upper opening of the housing and movable across a lower opening of the housing to abrade the delivery site in at least one furrow, and an abrader surface attached to the applicator head whereby the housing remains firm and stationary at the delivery site and structure of the housing and the applicator head controls parameters of the abrasion process. In particular, the amount of force or pressure applied to the abrader surface, the speed at which the abrader surface moves across the skin and the number of lateral passes of the abrader surface across the skin are controlled so that the abrader device provides a furrow with a length of substantially the same depth thereby providing reproducible results, even though different technicians are applying the abrader device against a patient's skin.

9 Claims, 9 Drawing Sheets

U.S. PATENT DOCUMENTS

| | | | |
|---|---|---|---|
| 5,843,114 A * | 12/1998 | Jang | 606/186 |
| 5,879,326 A | 3/1999 | Godshall et al. | |
| 5,964,729 A | 10/1999 | Choi et al. | |
| 5,983,136 A | 11/1999 | Kamen | |
| 6,050,988 A | 4/2000 | Zuck | |
| 6,083,196 A | 7/2000 | Trautman et al. | |
| 6,183,434 B1 | 2/2001 | Eppstein et al. | |
| 6,230,051 B1 | 5/2001 | Cormier et al. | |
| 6,256,533 B1 | 7/2001 | Yuzhakov et al. | |
| 6,322,808 B1 | 11/2001 | Trautman et al. | |
| 6,334,856 B1 | 1/2002 | Allen et al. | |
| 6,440,096 B1 | 8/2002 | Lastovich et al. | |
| 6,503,231 B1 | 1/2003 | Prausnitz et al. | |
| 6,537,242 B1 | 3/2003 | Palmer | |
| 6,537,264 B1 | 3/2003 | Cormier et al. | |
| 6,558,361 B1 | 5/2003 | Yeshurun | |
| 6,562,014 B2 | 5/2003 | Lin et al. | |
| 6,595,947 B1 | 7/2003 | Mikszta et al. | |
| 6,835,184 B1 * | 12/2004 | Sage et al. | 604/46 |
| 2002/0010412 A1 | 1/2002 | Eppstein | |
| 2002/0077584 A1 | 6/2002 | Lin et al. | |
| 2002/0091357 A1 | 7/2002 | Trautman et al. | |

FOREIGN PATENT DOCUMENTS

| | | |
|---|---|---|
| EP | 1 086 719 | 3/2001 |
| WO | WO 95/12357 | 5/1995 |
| WO | WO 96/17648 | 6/1996 |
| WO | WO 97/48440 | 12/1997 |
| WO | WO 02/02180 | 1/2002 |
| WO | WO 02/32331 | 4/2002 |

* cited by examiner

MICROABRADER WITH CONTROLLED ABRASION FEATURES

RELATED APPLICATIONS

This application claims priority to U.S. Provisional Patent Application No. 60/406,694, filed Aug. 29, 2002, which is hereby incorporated by reference in its entirety. This application is also related to U.S. application Ser. No. 10/649,134, and U.S. application Ser. No. 10/649,396, both filed concurrently herewith.

FIELD OF THE INVENTION

The present invention relates to a method for abrading the skin with controlled abrasion features. More particularly, the invention is preferably directed to a method of abrading the stratum corneum by forming furrows to promote delivery or sampling of a substance.

BACKGROUND OF THE INVENTION

The skin is made up of several layers with the upper composite layer being the epithelial layer. The outermost layer of the skin is the stratum corneum that has well known barrier properties to prevent external molecules and various substances from entering the body and internal substances from exiting the body. The stratum corneum is a complex structure of compacted keratinized cell remnants having a thickness of about 10-30 microns. The stratum corneum forms a hydrophobic membrane to protect the body from invasion by various substances and the outward migration of various compounds.

The natural impermeability of the stratum corneum inhibits the administration of most pharmaceutical agents, vaccines and other substances through the skin. Numerous methods and devices have been proposed to enhance the permeability of the skin and to increase the diffusion of various drugs through the skin. Typically, the delivery of drugs through the skin is enhanced by either increasing the permeability of the skin or increasing the force or energy used to direct the drug or vaccine through the skin.

Several methods of enhancing skin permeability have been proposed and used with varying success. One known method uses an adhesive strip that is repeatedly applied to the skin to strip numerous layers of cells from the stratum corneum. Other methods use a scraper such as a scalpel blade to abrade the skin. These methods are usually painful or uncomfortable and increase the risk of infection by excessively reducing the skin barrier function.

Another method of delivering medicaments including drugs through the skin is by physically forming micropores or cuts through the stratum corneum. This method delivers the medicament to the tissue below the stratum corneum, which can enhance the effectiveness of the medicament delivered. The devices for this use include micron-size needles or blades having a length sufficient to pierce the stratum corneum. Examples of these devices include those shown in U.S. Pat. No. 6,050,988 to Zuck; U.S. Pat. No. 5,879,326 to Godshall et al.; and U.S. Pat. No. 5,250,023 to Lee et al.; EP 0 381 410 and WO 97/48440.

The epidermis is a particularly desirable target for vaccine delivery as it is rich in antigen presenting cells. The dermis, in comparison, contains fewer antigen presenting cells (APC's). In addition, the epidermis and the stratum corneum do not contain nerves or blood vessels so this site has the advantage of being essentially painless and blood-free while giving access to the skin layers capable of responding to the antigen.

Techniques and devices for forming furrows in the stratum corneum exist which increase the surface area of the exposed epidermal layer and enhance absorption of a medicament including drugs and pharmaceutical agents or medicament into the body, also are known (EP 1 086 719). However, the technique therein involves lateral movement of the abrader device, which can introduce inconsistencies that vary with the technician, user or patient. The inconsistencies can include the dosage amount of the drug or vaccine and depth of the delivery site. In the past, devices have been proposed which aid in the proper perforation of the skin as in U.S. Pat No. 5,843,114 to Jang (herein referred to as '114). The '114 patent relates to disk perforator system including a switched light emitting diode to indicate proper pressure in a digital fashion.

Thus, there remains a need for a device that is consistent in both delivery of the vaccine, drug solution or other agent and the amount of abrasion to the patient's skin. Accordingly, a continuing need exists in the industry for an improved device for the epidermal administration of various drugs and other substances.

SUMMARY OF THE INVENTION

The instant invention is directed to a microabrader with controlled abrasion features and a method for using the same. The ability to monitor and thus control the amount of pressure or force applied to a microabrader results in a controllable and consistent abrasion to a desired area of skin. The method and controlled abrasion features promote consistency of the amount of abrasion even when different technicians are involved. This promotes uniformity in the dosage amount of a drug or vaccine delivered and consistency in the delivery site depth or the abraded area under the stratum corneum for absorption by the body.

A microabrader with controlled abrasion features may be used to apply a vaccine, drug solution or other agent by moving the microabrader laterally (back and forth) across an area of the skin forming furrows or grooves in which the vaccine, drug solution or other agent is to be delivered. In addition, a rotary motion associated with the abrader may be imparted through a handle on the abrader itself by the technician or through a mechanical rotary device. An array of microprotrusions are disposed on an abrading surface that is attached approximately perpendicular to a longitudinal axis of the abrader. The abrading surface is placed against the desired skin and the lateral or rotary motion can be used to treat the skin forming furrows or grooves prior to, simultaneously with or after drug or vaccine delivery. The lateral or rotary motion may be associated with actual medicament delivery if the drug or vaccine substance is pre-applied or coated on the surface of the microabrader array of the microabrader device.

A circular abrasion of the skin may be achieved with a mechanical or externally-powered rotary device including a microabrader device so that a localized area of skin is treated or abraded with an appropriate depth of furrows. The rotary device would comprise a housing in which the microabrader array is rotated against a subject's skin to form the furrows and an interlock mechanism that the user would deactivate to actuate the rotation of the rotary device. In one embodiment, the housing of the rotary device or a lateral abrader device would keep the skin in place as pressure is applied to ensure that the microabrader array surface would abrade and/or tension the same area of a patient's skin and a spring or other component associated with the interlock mechanism would control the pressure at which the microabrader surface moves against the skin. Consequently, this embodiment should ensure consistent, reproducible abrasion to the desired skin resulting in the same the amount of substance absorbed into a body, especially in clinical settings.

The circular abrasion formed by a manual microabrader or a rotary device can be combined with means for monitoring the amount of pressure applied to the microabrader device (e.g. visually) to maintain an approximate constant downward force to achieve a more consistent abrasion of the skin across the desired delivery area, and more efficiently deliver a vaccine, drug solution or other agent to a patient's body. For example, the technician and/or user can monitor the downward force being applied to the microabrader device during the lateral or rotary motion so that a consistent, downward force or pressure is applied resulting in an appropriate depth along the length of furrows being formed. Thus, the technician using the microabrader device can apply the necessary pressure to achieve the same degree of stratum corneum disruption and depth of penetration on all patients. It is also desirable to provide analog feedback to the user so that this necessary pressure can be maintained throughout the abrasion process. This may be especially important for delivery of certain classes of compounds, such as vaccines, in which the desired target area is the antigen-presenting cells within the epidermis and not the deeper dermal tissue and capillary beds. In this case it may be desirable to deliver the compound to the epidermis without piercing the epidermis.

This is achieved by an abrader device for delivering a substance into skin via an abrasion process that includes a housing adapted to be fixedly attached to or pressed against the skin at a desired delivery site, an applicator head disposed in an upper opening of the housing and movable across a lower opening of the housing to abrade the delivery site, and an abrader surface attached to the applicator head whereby the housing remains firm and stationary at the delivery site and structure of the housing and the applicator head controls parameters of the abrasion process. In other embodiments, the speed at which the abrader surface moves across the skin disrupting the stratum corneum is controlled, as well as the surface area or region to be abraded with furrows or grooves.

The monitoring of the pressure can be achieved via a mechanical or electrical pressure gauge, a pre-compressed (pre-loaded) spring, or an electronic pressure transducer. This monitoring device may be as simple as indicia or as sophisticated as an electronic piezoelectric film that detects the amount of pressure and indicates the amount of pressure. In addition to the amount of downward force applied to the microprotrusions when positioned over the skin, other parameters, such as the speed at which the microprotrusions pass laterally over the skin surface and the number of lateral passes of the microprotrusions across the skin, may be controlled to provide optimum reproducible abrasion of the desired area of the skin.

According to other embodiments of the invention, the application of rotary or lateral motion to a microabrader array surface would occur inside a housing, which is held against the skin to be abraded and the abrader surface would be moved within the relatively stationary housing so that the microabrader array surface would effectively abrade that one area of skin forming furrows of an appropriate depth. The abrader surface being moved laterally or rotary within a housing should result in better control of the area of skin to be abraded. The microabrader device with a housing could also have a spring mounted therein to maintain a constant downward force and thus pressure applied to the abrading surface of the microabrader device thereby allowing an appropriate depth of penetration of the abrader surface along the desired skin site to form the furrows. Both the housing and means for providing a constant application force upgrade the functionality of the manual microabrader by improving uniform skin tension, a constant skin treatment area and a constant application of pressure or force to the abrading surface, even when different technicians use the microabrader device.

In yet another embodiment, the housing could serve as a safety device within which a single-use microabrader array surface can be retracted after abrading the skin. For example, this safety feature can be achieved with a retraction detent in the housing of the rotary device or a cushion layer in the housing, which can secure the microabrader array surface within the device for safe disposal.

BRIEF DESCRIPTION OF THE DRAWINGS

The invention is better understood by reading the following detailed description with reference to the accompanying figures, in which like reference numerals refer to like elements throughout, and in which.

DETAILED DESCRIPTION OF THE INVENTION

The present invention is directed to a device and to a method for abrading the stratum corneum with controlled abrasion features in either a lateral or a rotary fashion to enhance the administering of a substance through the stratum corneum of the skin of a patient.

As used herein, the term abrade refers to removing at least a portion of the stratum corneum to increase the permeability of the skin without causing excessive skin irritation or compromising the skin's barrier to infectious agents. This is in contrast to "puncturing" which produces discrete holes through the stratum corneum with areas of undisrupted stratum corneum between the holes.

The term "penetrating" in this application is defined as entering the stratum corneum without passing completely through the stratum corneum and entering into the adjacent layers. This is not to say that the stratum corneum cannot be completely penetrated to reveal the interface of the underlying layer of the skin. Piercing, on the other hand, refers to passing through the stratum corneum completely and entering into the adjacent layers below the stratum corneum.

The primary barrier properties of the skin including the resistance to drug or vaccine delivery reside in the outermost layer of the epidermis, referred to as the stratum corneum. The inner layers of the epidermis generally include three layers, commonly identified as the stratum granulosum, the stratum malpighii, and the stratum germinativum. Once a drug or vaccine or other substance appears below the stratum corneum, there is essentially no resistance to diffusion into subsequent layers of the skin and eventual absorption by the body.

Delivering a substance into or through the viable epidermis can be an effective method for facilitating absorption of some substances, and particularly some vaccines, by the body. The present invention is primarily directed to a device and method for facilitating delivery of a substance, and particularly a pharmaceutical agent, into or through the viable epidermis so that more rapid absorption of larger quantities of the bioactive substance or pharmaceutical agent results.

The rotary method and the device for rotating a microabrader array surface according to one embodiment of the invention is capable of abrading the skin to increase the exposed surface area within the epidermal layer and improve the efficacy of substance or drug or vaccine delivery into the body of the subject by either direct uptake by the antigen presenting cells (APC's), capillary drainage, or the lymphatic drainage phenomenon. In preferred embodiments, the device is capable of abrading the skin thereby penetrating the stratum corneum without piercing the stratum corneum.

An abrading surface with a desired array of microprotrusions is either rotated or laterally moved across against a desired skin area. The resultant abrasion of the skin according to the invention disrupts the stratum corneum increasing the surface area of the viable epidermal layer so that a greatly increased dose concentration of the substance delivered is achieved. In the circular motion embodiment, the abrasion tends to keep the dose within the rotary or circular abraded area. Consequently, the dose can be limited to a smaller area of abrasion by using the circular or spin delivery according to one embodiment of the invention resulting in increased substance delivered to a limited portion of the body. Depending upon the subject or the substance being delivered, a smaller or larger abrading area may be used and delivered by using the circular motion technique or a straight technique, respectively.

The substance to be administered using the methods of this invention may be applied to the skin prior to abrading, simultaneous with abrading or post-abrading. According to one embodiment of the methods of the invention, however, certain or specific bioactive substances, including nucleic acid-based vaccines and peptides or polypeptides, are applied to the skin prior to or simultaneously with abrasion rather than being applied to previously abraded skin. That is, certain substances when abraded into the skin rather than being passively applied to previously abraded skin result in improved response.

The substance may be delivered into the skin in any pharmaceutically acceptable form. In one embodiment, the substance is applied to the skin and an abrading device is then forced against the skin while being twisted or moved in a lateral fashion over the skin and the substance. It is preferred that the minimum amount of downward force to produce the abrasion that achieves the desired result be used. The amount of force and lateral or circular motion to achieve the necessary abrasion to achieve efficient delivery depends upon the drug or vaccine to be delivered. One of ordinary skill in the art would be able to determine the appropriate amount of force and motion (and thus, the resultant abrasion) to achieve the appropriate amount of drug or vaccine delivery through routine experimentation.

In another embodiment, the substance may be applied in dry form to the abrading surface or an adjacent surface thereto of the delivery device prior to application. In this embodiment, a reconstituting liquid is applied to the skin at the delivery site and the substance-coated abrading device is applied to the skin at the site of the reconstituting liquid. It is then twisted against or rubbed in a lateral fashion over the skin so that the substance concurrently or subsequently becomes dissolved in the reconstituting liquid on the surface of the skin and is delivered simultaneously with abrasion. Alternatively, a reconstituting liquid may be contained in the abrading device and released to dissolve the substance as the device is applied to the skin for abrasion. Due to the containment of the abrader in a smaller area when using a twisting or circular abrading motion, the volume of reconstitution liquid may also be reduced.

According to the invention, skin disruption, for example, furrows or other openings will be formed when the microabrader is moved across the desired area of skin. If the microabrader abrading surface area is composed of a rectangular, square or other arrays of microprotrusions and a twisting or circular motion moves the abrader, intersecting furrows result. This intersection of furrows suggests that the reconstituting liquid will have more grooved areas within the abraded area and thus may minimize the amount of liquid lost due to the centrifugal force of the rotating microabrader abrading surface. In addition to the greater amount of furrows in the abrading skin, a more tortuous path is created which likewise suggests the liquid will tend to remain in the abraded area. Thus, the circular abrasion method can employ a lower volume of reconstitution liquid and suggests a reduction of substance loss since the abrader will form furrows that capture the substance thereby avoiding the urging away of the substance as known in prior abrading methods.

Figure 1:
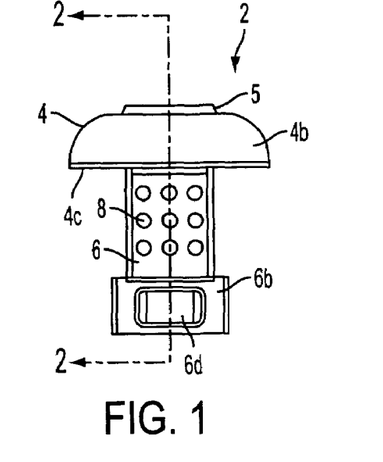
FIG. 1 is a side view of a microabrader that can be applied manually.
Figure 3:
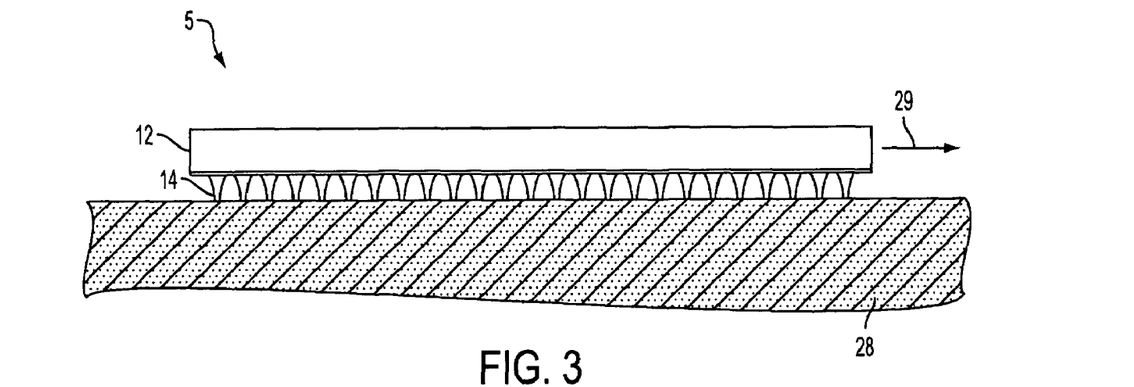
FIG. 3 is an exploded side view of an abrading surface for an abrader array according to the invention on the skin of a patient.
Figure 4:
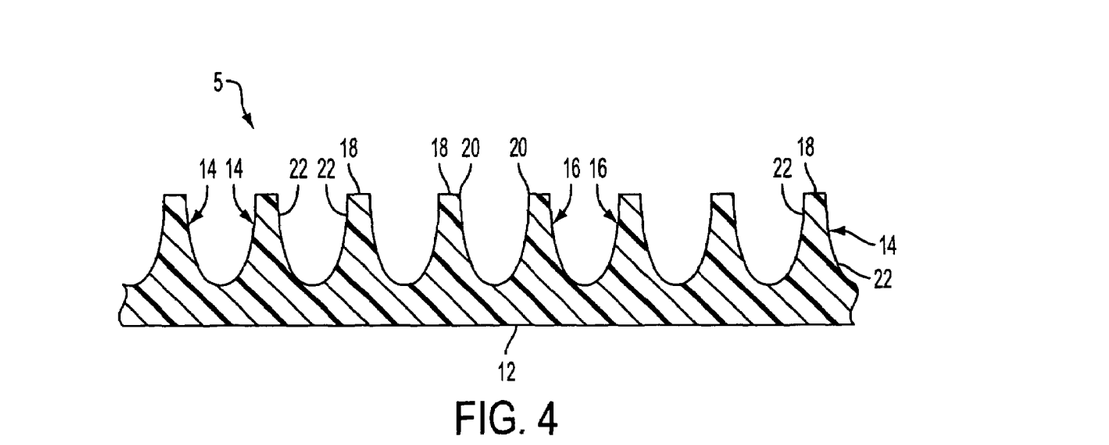
FIG. 4 is a cross sectional side view of an abrading surface.
Figure 5:
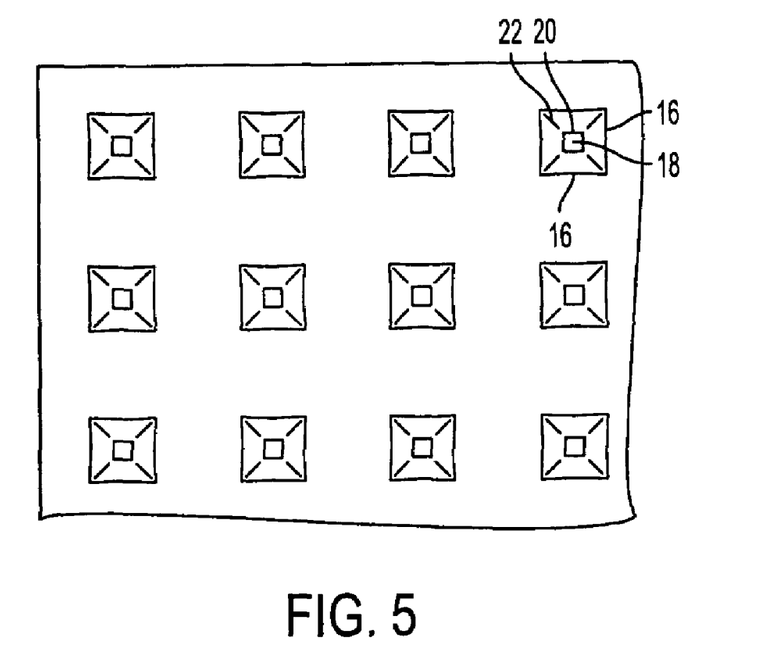
FIG. 5 is a bottom view of the abrading surface of the embodiment of FIG. 3.

As shown in FIG. 1, a manual microabrader device 2 includes base 4 onto which an abrading surface 5 can be mounted. Preferably, base 4 is a solid structure made of metal or plastic. In one embodiment, base 4 is configured with a mushroom-like crown 4b that curves upward and is truncated at the top. The top of base 4 is generally flat with abrading surface 5 being mounted thereon. Alternatively, the truncated top may have a recess for receiving abrading surface 5. In all embodiments, abrading surface 5 includes a platform 12 with an array of microprotrusions 14 (FIG. 3) that extends above the truncated top. In exemplified embodiments, the protrusion or needlelike arrays are frustoconical as shown in FIG. 4 and may be made of approximately pyramidal mesas as shown in FIG. 5 of the instant invention. The frustoconical shape of the protrusions controls the depth of the abrasion by the abrading surface. As stated above, the array of microprotrusions can be rectangular, square, circular or any shape, including blades, that promotes delivery of a substance into a body.

Microabrader device 2 of FIG. 1 is applied to a subject by moving microabrader device 2 in a lateral (or circular) motion against a subject's skin 28 (arrow 29) with enough pressure to enable abrading surface 5 to penetrate the outer protective skin or stratum corneum of the subject. The pressure applied to the base causes surface 5 and base 4 to be pressed into the subject's skin. Accordingly, it is preferred that the height of the sloping mushroom-like crown 4b be sufficient to prevent an applied substance from flowing over and onto underside 4c of base 4 when microabrader device 2 is being used.

A handle 6 is attached to arcuate base 4. An upper end 6c of handle 6 may be either snap fit or friction fit between the inner circumferential sidewall 4a of base 4. Alternatively, handle 6 may be glued (e.g., with epoxy), or may be a snap or friction fit, or be integrally molded to the underside 4c of base 4. Underside 4c of base 4 may be flush with mushroom-like crown 4b or extend beyond the mushroom-like crown. The lower end 6b of handle 6 is wider than the shaft of handle 6. Lower end 6b includes an impression 6d that serves as a thumb rest for a person administering the substance and twisting microabrader device 2. In addition, protrusions 8 are formed on the outside of handle 6 to assist a user in firmly gripping handle 6 when twisting the same against a patient's epidermis.

Figure 2:
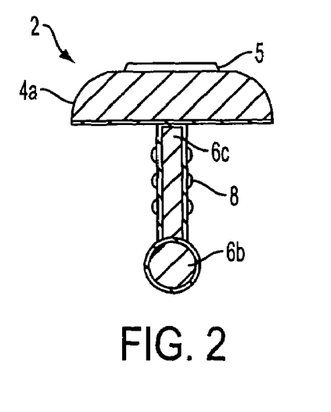
FIG. 2 is a cross sectional view of the microabrader of FIG. 1.

As shown in the cross-section of FIG. 2, lower end 6b may be cylindrical. Impressions 6d are disposed on both sides of the cylindrical lower end 6b to assist a person using microabrader device 2 to grip the same. That is, the movement of microabrader device 2 can be provided by hand or fingers, or by interconnection with a rotary device. The handle 6, as well as the base 4, of the microabrader device 2 is preferably molded out of plastic or the like material. The microabrader device 2 is preferably inexpensively manufactured so that the entire microabrader device and abrading surface can be disposed after its use on one patient.

One method of forming an abrading surface with microprotrusions is by etching a rectangular piece of silicon. The etching procedure provides a master abrading surface with a surface contour. As described below, the master abrading surface can become a mold for an abrading surface with an array of microprotrusions. The surface contour of the master is coated with a layer of material, the layer preferably having a thickness of at least about 0.01-0.2 inches and preferably 0.07 inches or greater. The master is removed from the layer of material to form a negative image of the master in the layer of material. The negative image may then be used in a molding process to form a positive image having features that are substantially the same as the features of the master.

The master is sacrificed when it is removed from the layer of material. For example, the master may be removed by etching. In another embodiment, the master is coated with a release layer, before being coated with the layer of material. The release layer facilitates removal of the master from the negative image, preserving the master unharmed.

Another method of forming an abrading surface with a plurality of microprotrusions involves using a master abrading surface having a surface contour defining a plurality of features. The surface contour of the master is coated with at least one layer of material to form a shell. The master is removed from the shell to form a negative image of the surface contour in the shell. The negative image in the shell is substantially filled with material, for example, polycarbonates (LEXAN® polycarbonate), acrylics (ACRYLITE® acrylic), COCs (Topas® Cyclic-Olefin Copolymers), polystyrenes, or other suitable structural plastic, to form a device having features substantially the same as the master. Of course, other types of materials may be used to fill the shell. The negative image may be filled using injection molding, compression molding, embossing or any other compatible technique.

In a further embodiment, the shell defines recesses having a depth of about 5 microns to about 250 microns. The recesses may be arranged in an array of uniformly spaced or non-uniformly spaced rows and columns or other patterns, including random patterns, to provide a density of about 4 to about 100 of the recess per $mm^2$. The shell is a negative or reverse image for molding the features of the master, where the master can have recesses or peaks on its surface contour ranging from about 0.5 micron to several hundred microns in length.

As described above, a method for delivering a substance into the skin of a patient can include the steps of coating a patient's outer skin layer with a vaccine, drug solution or other agent and moving microabrader device 2 against the patient's skin to provide abrasions leaving furrows sufficient to permit entry of the substance into the patient's epidermis. Alternatively, the vaccine, drug solution or other agent may be applied to abrading surface 5 of microabrader device 2. If desired, rotation may be manually performed by twisting the wrist of the technician holding microabrader device 2, or, achieved mechanically or electronically with a device (FIGS. 7-8) that rotates the microabrader device as described below. The rotation or twisting may be performed in either the clockwise and counter-clockwise direction, or both directions.

Figure 6:
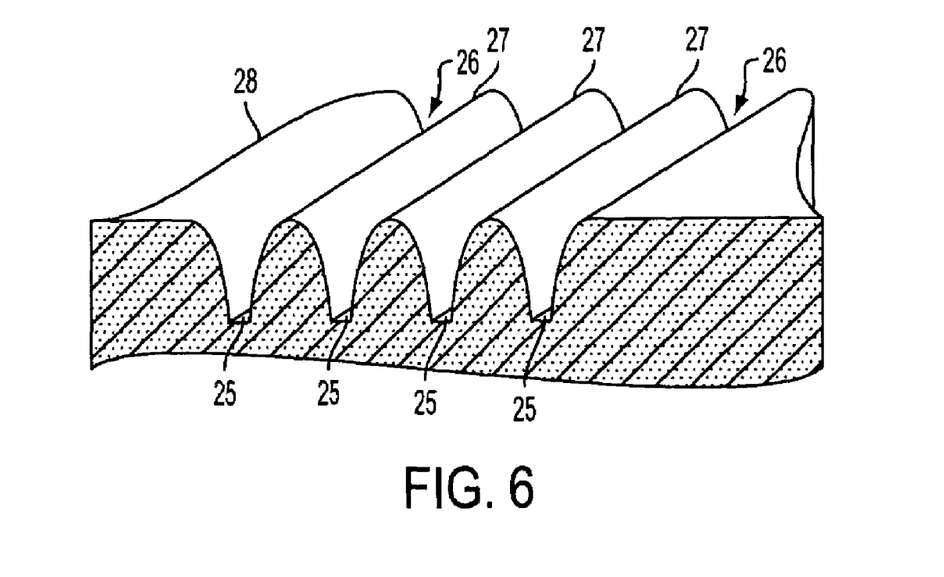
FIG. 6 is a perspective view in partial cross section of abraded furrows of skin.

Due to the structural design of microabrader device 2, the leading arcuate base of a preferred microabrader device 2 stretches the patient's skin and then the top surfaces or edges 20 (FIG. 4) of microprotrusions 14 abrade the outer protective skin layer by penetrating the stratum corneum forming grooves 26 thereby permitting medicament or other substance to enter the patient. In addition to edges 20, edges 22 of microprotrusions 14 also form scraping edges to aid in forming the grooves 26 or furrows in skin 28. As shown in FIG. 6, depending on the number of microprotrusions 14 and their arrangement on abrading surface 5, scraping edges 20 and 22 form open valleys 25 and scarified side walls 27 in the grooves 26. After the initial abrasion of the outer protective skin layer in a first circular direction, the trailing and leading edges of microabrader device 2 may also rub the surface of the abraded area working the vaccine, drug solution or other agent into the abraded skin area thereby improving its interaction with the underlying epidermis.

Figure 7A:
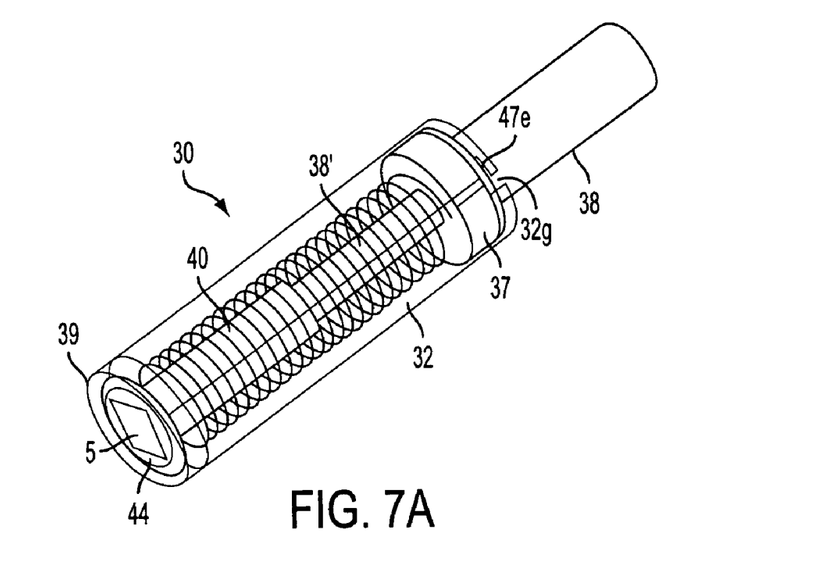
FIGS. 7A-B and D illustrate rotary delivery devices according to the invention that control the abrasion process.
Figure 7B:
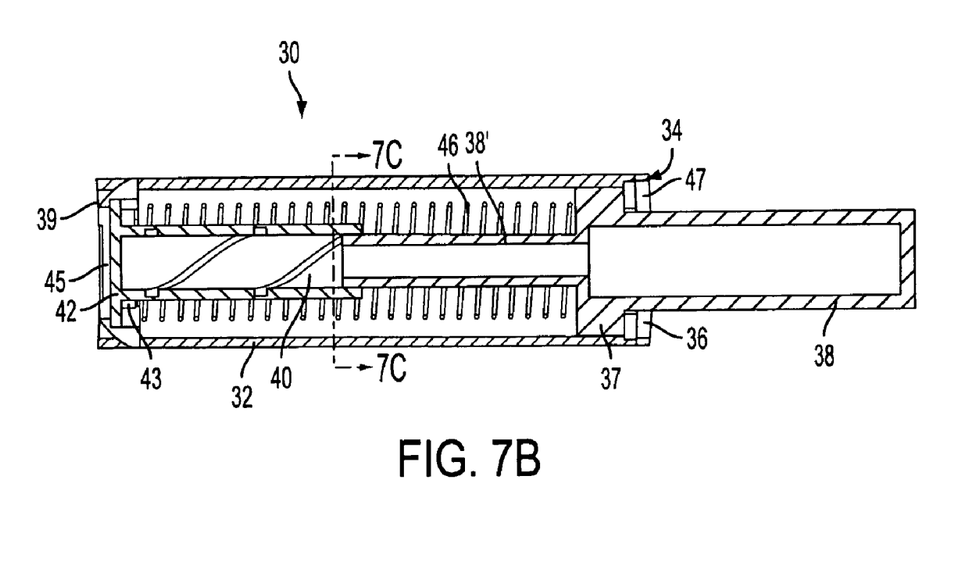

Looking at FIGS. 7A and B, a rotary delivery device 30 is shown according to one embodiment of the invention. FIG. 7A is a perspective view of a device depicted with a see-through housing so that the mechanical components can be viewed, while FIG. 7B is a sectional view of rotary device 30. Rotary delivery device 30 includes a housing 32, which is cylindrical in this preferred embodiment. The housing need not be circular, as rectangular, square, oval or other shapes may be used. Housing 32 has a longitudinal axis, is generally hollow and is preferably of a shape about which a user's fingers can grasp for added control. The top 34 of housing 32 has an opening 36 through which an interlock mechanism, such as button 38 that is integrally attached to a longitudinally movable rod 38', moves upon activation. In a preferred embodiment, the top of button 38 extends through opening 36 while a base 37 of button 38 adjacent rod 38' is located inside housing 32. Base 37 has a larger width/diameter than the top of the base. The width/diameter of the base is approximately equal to the interior of housing 32. The thickness of base 37, as well as its width, is designed to provide a strong, stable support for the activation means or push button 38. Rod 38' is integrally attached to the base 37 of button 38 inside of housing 32.

The other end 39 of rotary delivery device 30 is designed to be placed against a subject's skin and to remain stationary while button 38 is activated. Thus, end 39 of housing 32 serves to tension the skin of a subject prior to abrasion by an abrading surface 5. That is, the perpendicular force applied to the rotary delivery device provides a tight skin area to aid the abrading surface in scraping the skin area.

Located concentrically inside housing 32 and preferably recessed from end 39 of rotary delivery device is a hollow sleeve 40. Hollow sleeve 40 is freely rotatable within housing 32 and is formed with groove-like threads. The end of longitudinally movable rod 38' opposite the end attached to button 38 is inserted into the top end of hollow sleeve 40. Projections (FIG. 7C) extending from the end of longitudinally movable rod 38' extend into groove-like threaded areas 41 of hollow sleeve 40. The threads are designed to transfer the longitudinal movement of button 38 and rod 38' into a rotary movement. Alternatively, the opposite end of rod 38' could be provided with a recess and hollow sleeve 40 could have raised threads in order to translate the longitudinal motion of rod 38' into the desired rotary movement. As a result of this structure, when button 38 is activated, the projections of rod 38' collapse inside hollow sleeve 40 along the thread grooves thereby causing hollow sleeve 40 to spin approximately 360 degrees through the full stroke of button 38.

An end face 42 is integrally formed at the end of hollow sleeve 40 near end 39 of rotary delivery device 30. In an alternative embodiment, an end face may be attached via adhesive or the like to hollow sleeve 40. An abrading surface 5, such as previously described, is attached to a front end 44 of face 42 of hollow sleeve 40. Thus, abrading surface 5 can be retracted inside housing 32 before button 38 is pressed or activated. The groove-like thread parallel to the longitudinal axis allows hollow sleeve 40 and abrading surface 5 to be recessed. The curved portion of the groove-like threads can be designed so that the abrading surface 5 rotates approximately 360 degrees against a subject's skin when button 38 is depressed. Depending upon the drug or vaccine to be delivered, less rotation or multiple rotations of abrading surface may be desired. Since housing 32 remains relatively stationary while button 38 is activated, housing 32 keeps the skin in place as abrading surface 5 abrades the area of skin inside stationary housing 32. Consequently, consistent, reproducible results as to the amount of drug or vaccine absorbed by a patient should be achieved by rotary delivery device 30.

While the interlock mechanism illustrated is a button disposed perpendicularly to the abrading surface, other interlock mechanisms may be employed. For example, a lever disposed about the housing of the rotary device may be pushed approximately parallel to skin held in place by the housing. The lateral pushing of the lever would deactivate a spring causing the abrading surface 5 held within the housing to rotate. Similarly, a handle projecting from the side of the housing may be a lever, button or rotary motion device that deactivates the spring causing the abrading surface 5 to rotate.

Abrading surface 5 may be attached to front end 44 of hollow sleeve 40 via a ring 45, as shown in FIG. 7B or can be directly attached to front end 44 of hollow sleeve 40 via adhesive (FIG. 7A). As rod 38' collapses inside hollow sleeve 40, the projections follow the threads of hollow sleeve 40 so that hollow sleeve 40 and abrading surface 5 are rotated due to the threaded hollow sleeve. Thus, as the button 38 is pushed, the abrading surface 5 rotates against the subject's skin. The abrading surface 5 may be permanently attached to a disposable piece, or, the abrading surface may be disposed on a chip that can be snapped onto the ring 45 or another disposable piece. This will enable the chip to be replaced without having to reproduce the entire rotary delivery device.

In another embodiment, the abrading surface 5 may also be made integral with end face 42 attached to hollow sleeve 40. In such an embodiment, the entire rotary delivery device would be disposable after abrading a single patient. It is envisioned that rotary delivery device 30 may be employed to abrade more than one location on a single patient to deliver a vaccine or other substance and then the rotary delivery device 30 can be disposed. It is also envisioned that the rotary device be modified to adapt to or otherwise mate with or accept a separate microabrader device instead of having the abrading surface 5 integral therewith.

A pre-compressed spring 46 concentrically surrounds the rod 38' and hollow sleeve 40. As shown in FIG. 7B, end face 42 of hollow sleeve 40 has a projecting rim 43 and spring 46, in its extended state, extends from projecting rim 43 to base 37. The depression of button 38 compresses spring 46 so that device 30 will automatically reset when pressure is removed from button 38. That is, when button 38 is no longer depressed thereby releasing spring 46 from its compressed state, spring 46 applies an opposite load causing abrading surface 5 to rotate 360 degrees in the opposite direction. Button 38 can be pushed a number of times depending upon the amount of abrasion desired. This retracted abrading surface provides a safety disposal feature for the rotary delivery device.

Figure 7C:
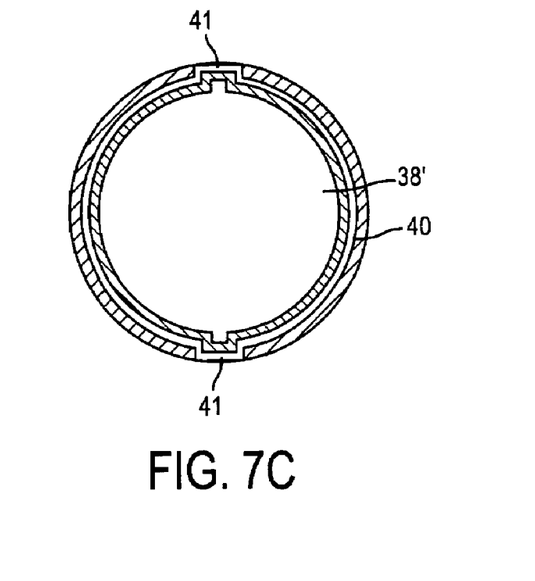
FIG. 7C is a cross-section through 7C-7C of FIG. 7B.
Figure 7D:
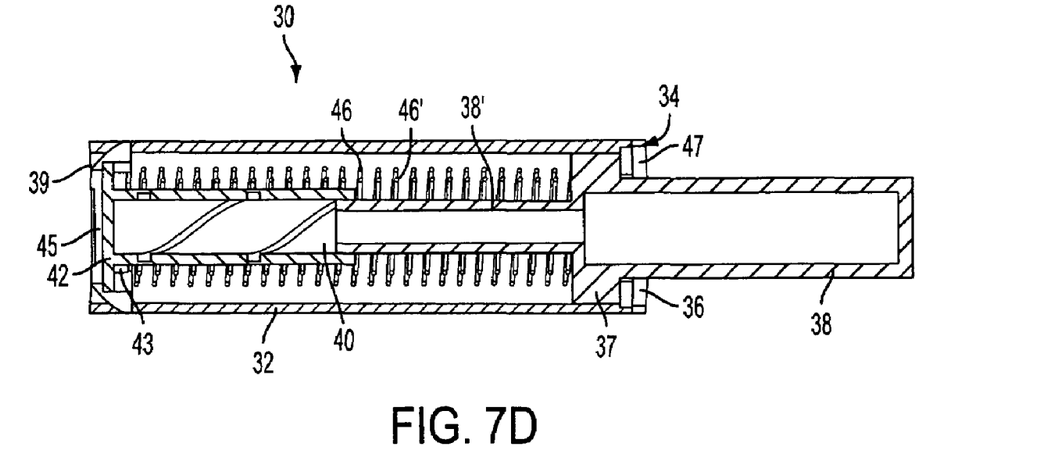
Figure 7E:
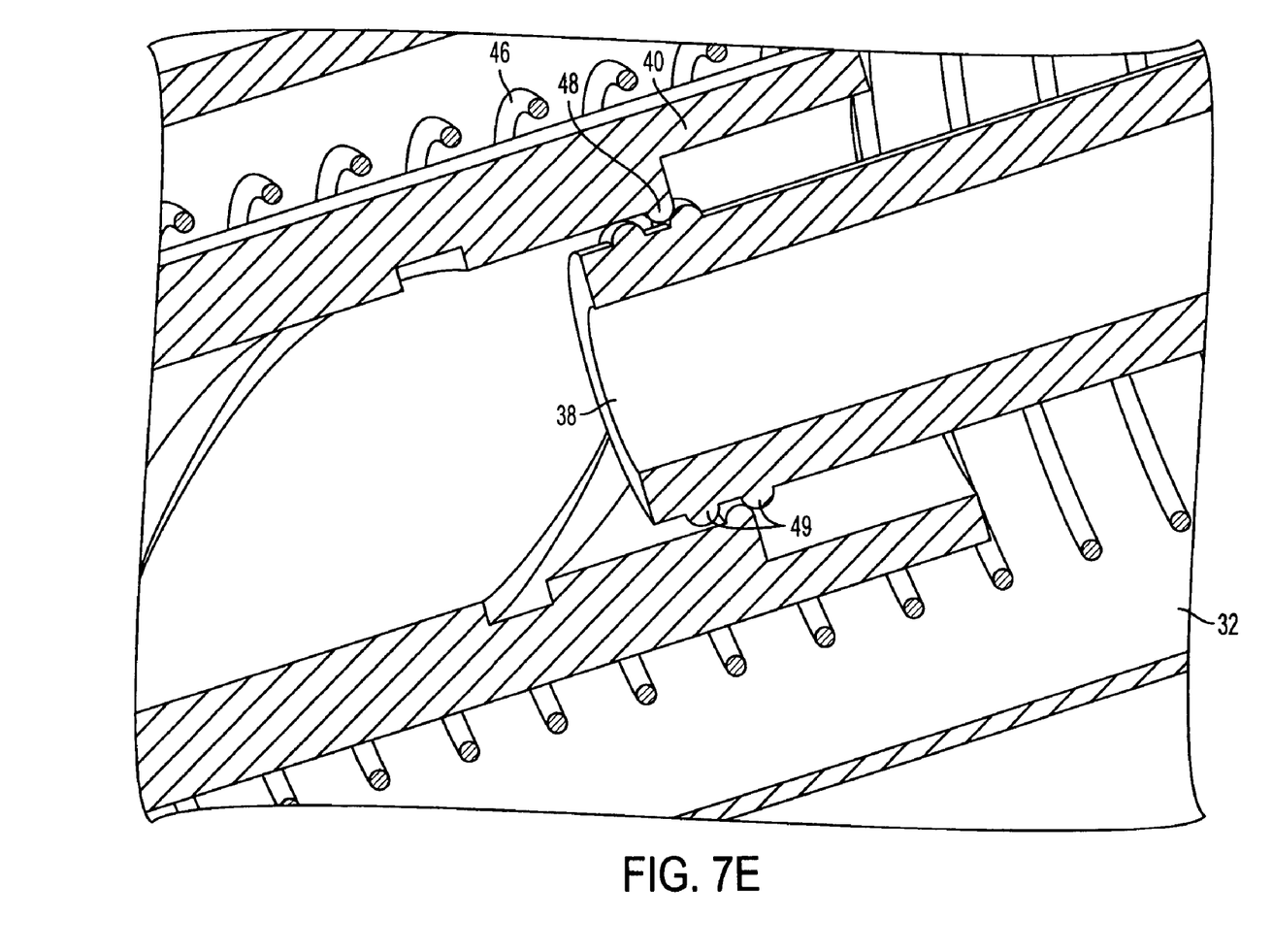
FIG. 7E is an exploded, cross-sectional view of a movable rod and hollow sleeve of a rotary device according to an embodiment of the invention.

FIG. 7E illustrates one embodiment according to the invention in which the end of rod 38' and top of hollow sleeve 40 are designed to provide a safety retraction feature. The top of hollow sleeve 40 is provided with a projecting lip 48 and the end of rod 38' is provided with two projecting lips 49 that are spaced from one another. After the rotary delivery device has sufficiently abraded the desired area of skin, an operator pulls button 38 away from housing 32 causing one of the projecting lips 49 of rod 38' to move past projecting lip 48 of hollow sleeve 40 so that projecting lip 48 rests between the two spaced projecting lips 49 of rod 38'. In this manner, the hollow sleeve is pulled back within housing 32 and locked into this retracted safety position, as a large force would be necessary to move the hollow sleeve from the retracted safety position. An alternative embodiment is described below where a larger second spring could retract the entire abrading surface inside the housing 32.

For easy assembly of a rotary delivery device according to the invention, a retaining ring or washer 47 covers opening 36. In one embodiment, retaining ring 47 has two ears 47e on opposing sides of the ring, one of which is shown in FIG. 7A. Ears 47e are received in grooves 32g at the top of housing 32 and are locked in place by turning the same. In another embodiment, the top of housing 32 would be provided with a cap with an opening that receives button 38. The cap would be screwed onto housing 32. Thus, one could easily assemble spring 46, hollow sleeve 40, rod 38' and button 38 inside housing 32 and then lock the assembly together. Retaining ring 47 or a screw cap would hold the above components inside housing 32, even when spring 46 was released. The housing 32, hollow sleeve 40, rod 38' and button 38 are made from a plastic material, which can be easily molded into the particular shapes.

Figure 8A:
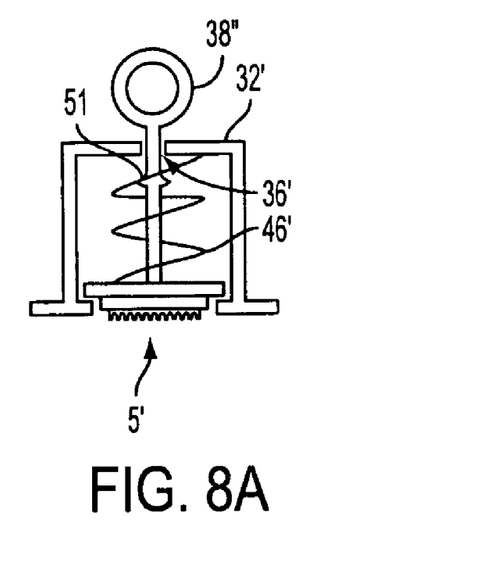
FIGS. 8A and 8B schematically show a detent 51 formed at the bottom of the push button of a delivery and retraction device.
Figure 8B:
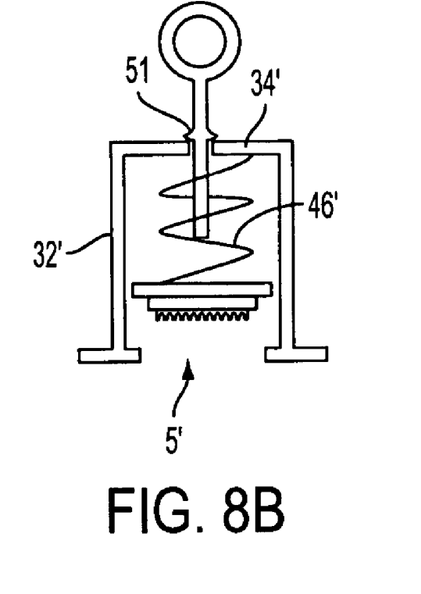

In another embodiment, means are provided for retracting the abrading surface within the rotary or a lateral (described below) delivery device. For example, a detent 51 formed at the bottom of button 38" may be used to secure the abrading surface within the housing after the desired amount of abrasion is achieved. In a preferred embodiment, detent 51 is sufficiently far away from the housing 32' so that it does not engage housing 32' during the abrasion process. This embodiment is schematically illustrated by FIGS. 8A and 8B. A coupler is used to mate a microabrader device with a handle to button 38" and housing 32'. In addition to mating a handle for lateral movement, any type of coupler is envisioned that can join the handle of a microabrader device with a button that can be rotated within a housing. The size of the detent 51 compared to the opening 36' is designed to ensure that a technician or user applying the microabrader device sufficiently retracts button 38" through opening 36', as illustrated in FIG. 8B.

In one embodiment, abrading surface 5' rests on a shoulder projecting from a bottom of housing 32', and a spring 46' is slightly compressed between the abrading surface 5' and the top of housing 32'. When a force is applied to housing 32', pre-compressed spring 46' retracts a slight distance as the force goes through housing 32' and abrading surface 5'. The pre-compressed spring 46' has a spring value that limits the amount of force sent through to abrading surface 5'. In addition, the spring is preloaded so that it will deflect only if the pressure required to penetrate the stratum corneum is exceeded. The spring rate is chosen so that the abrading surface can retract into the housing 32' instead of raising the pressure (or force) significantly above the predetermined force necessary to produce sufficient abrasion. The remainder of the force is sent through housing 32'. Consequently, if more force than necessary is applied against housing 32', the amount of abrasion remains constant. As a result, the pre-compressed and/or pre-loaded spring 46' controls the amount of pressure during the abrasion operation so that the appropriate amount of abrasion results across the subject's skin forming furrows or grooves 26 of the appropriate depth.

For example, if a force of 10 pounds is required to make a microabrader function properly, housing 32' holds a spring 46' that is preloaded at 10 pounds. The spring rate is 1 pound per mm so that the abrader deflects 1 mm if the force rises to 11 pounds. At the 1 millimeter deflection point, the abrading surface 5' is fully retracted within the device. After the skin has been abraded by abrading surface 5', a technician or user would release the pressure applied to the abrading surface and spring 46'. This release of the pressure may cause the abrading surface 5' to relax outside of housing 32'. In order to pull abrader surface 5' completely within housing 32', a technician or user would have to pull detent 51 through opening 36' of top 34' of housing 32'. This is a safety feature according to the invention, as the abrading surface of the delivery device would be retracted securely inside housing 32' and thus, the abrading surface remains retracted for safe disposal.

Applicants have determined through experiments that in order for the microabrader device to work properly and to deliver the appropriate dose of substance or medicament to within the epidermal layer of a patient, sufficient control of the amount of pressure applied to the microabrader device is required. According to the invention, the microabrader array surface 5 should only disrupt the stratum corneum. If too much pressure is applied, the microabrader device may remove too much of the epidermal layers. On the other hand, if not enough pressure is applied, the microabrader surface may not penetrate the stratum corneum. This under abrasion may result in not enough substance or medicament being delivered to the body. Control of the pressure being applied aids in determining the depth of penetration along the resultant grooves 26, as well as the amount of force to achieve the desired penetration and the desired abrasion.

The manual microabrader device described with reference to FIGS. 1-2 may be modified so that handle 6 includes a printed-matter gauge and incorporated into a device as shown in the perspective view of FIG. 9. In one embodiment of the invention, the printed matter gauge uses protrusions 8 as an indicator of the pressure being applied with a device of the present invention. Protrusions 8 may be color coded, or of different shapes to be used as an indicator. Preferable, protrusions 8, are replaced with a printed matter gauge which may be digital as in the case of 3 distinct colors or alternatively, analog in nature such as the case with color-coded gradients corresponding to the force being applied. The microabrader device of FIG. 9 may be made of a material that is opaque so that the printed-matter gauge can be hidden as described below. Alternatively, the material can be see-through, such as transparent or translucent plastic. As a result, the inner mechanisms of this device in this figure can be seen. In this embodiment, handle 6' would be longer than that of the microabrader shown in FIGS. 1-2. Handle 6' may have a post 6p, a spring 6s, and an upper portion 6u that collapses onto a lower portion 61 of the handle. Spring 6s surrounds post 6p, while lower portion 61 surrounds spring 6s and post 6p, and upper portion 6u surrounds an upper portion of lower portion 61. The upper part of post 6p may have a flange end that holds upper portion 6u together with lower portion 61. In a preferred embodiment, a screw-cap 6c threaded onto the end of post 6p and disposed adjacent upper portion 6u serves to securely keep handle 6' together. Upper portion 6u surrounds post 6p, moves up and down post 6p depending upon the amount of pressure applied to upper portion 6u. The upper portion 6u may have a window 7 through which printed indicia, printed matter gauge, or protrusions 8 on post 6p can be seen.

The spring 6s has a predetermined spring value that relates to the printed-matter gauge. For example, spring 6s may be a linear compression spring and post 6p may have a color-coded displacement scale which indicates the amount of pressure applied to the abrading surface 5". Depending upon the embodiment, the printed matter, which may be color-coded or symbols, is printed on the lower portion 61 of the handle either below upper portion 6u or on post 6p. In an embodiment where the printed matter is underneath upper portion 6u on post 6p, the technician applies pressure to the upper portion 6u causing the upper portion to move toward the abrading surface 5" moving window 7 which reveals the printed matter on the post. That is, the upper portion 6u would slide over the lower portion 61 so that the technician would be able to control the pressure applied to the microabrader moving across the patient's skin by observing printed matter on the post 6p. Alternatively, the printed mater may be disposed on the lower portion 61 of handle 6'. If the printed matter is color-coded, three different colors representing not enough pressure (e.g. yellow), too much pressure (e.g., red) or the appropriate pressure (e.g., green) may be employed. This provides an advantage in that the under pressure condition, as well as the over pressure condition is communicated to the technician or user. Alternatively, a single color or symbols may be used that represents the appropriate range of pressure.

In an alternative embodiment, post 6p protrudes from the top of the microabrader device and the printed matter on the post is revealed as the technician or user pushes down on spring 6s. That is, the amount of collapse of upper portion 6u is directly proportional to the force applied to the microabrader device. For example, as the downward force is applied, the upper potion 6u collapses on spring 6s and the post 6p will protrude in a manner proportional to the force. If the force applied is too light, the yellow band will be revealed at the top of the device. The technician or user will visually see this feedback and know to apply more force until the green band (representing the correct force range) shows. If the red band shows, the technician will know that too much force was being applied and lighten up on the microabrader device until the green band is revealed. Thus, with this direct, visual feedback, a technician or user of a microabrader device will be able to regulate the amount of force applied to the device resulting in consistency of the applied amount of pressure to the microabrader surface moving across the patient's skin to form furrows or grooves of an appropriate depth along their length. Consequently, different users of the microabrader device can use the feed back to deliver the same amount of pressure and resulting abrasion so that the efficacy of drug or vaccine delivery remains consistent.

Figure 9:
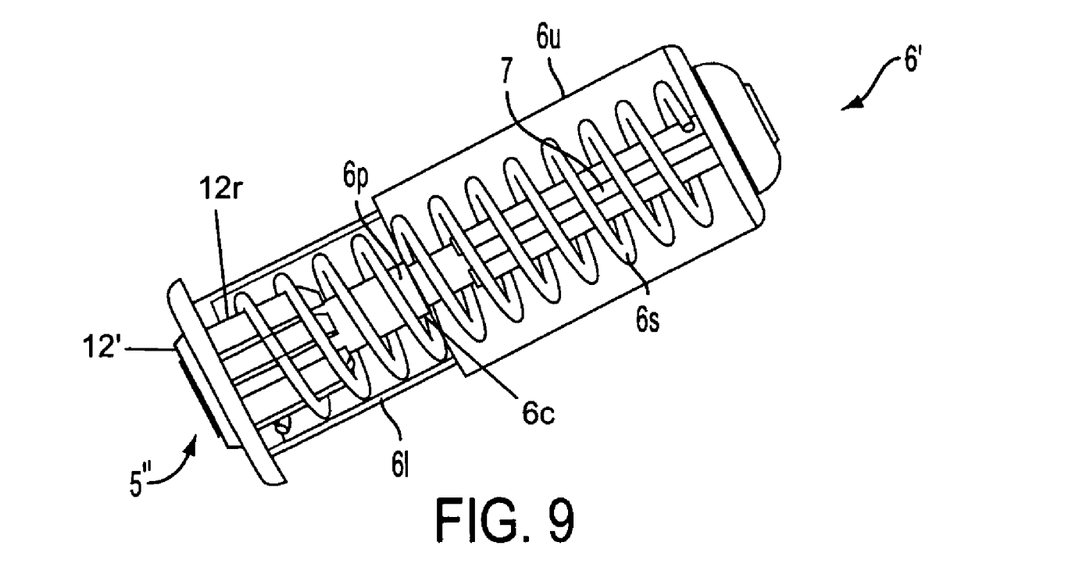
FIG. 9 illustrates a manual abrader with a pressure gauge according to the invention.

Looking at FIG. 9, the microabrader device has a flat abrading surface 5" that can be affixed via adhesive to a flat front surface 12'. The reverse side of flat front surface 12' has a number of ribs 12r projecting therefrom. The ribs 12r are designed to center and support displacement spring 6s. A preferred target constant of the spring value for spring 6s is about 6 lbs/inch, which yields approximately 3-4 lbs. of pressure when displaced 0.5-0.75 inch. This is the preferred mode with a flat square microabrader array that is to be moved laterally. Non-linear spring values are envisioned for some applications. Larger spring values (linear or non-linear) may be used to achieve the desired control of pressure for differing applications. In addition, Depending upon the drug or vaccine to be delivered to the patient, a differing amount of abrasion may be desired. According to the invention, the force range of the microabrader device is easily adjustable as the displacement spring can be replaced by unscrewing screw-cap 6c to reveal post 6p and to replace spring 6s. Thus, one could easily replace the internal spring with a different spring force profile and/solid height.

An alternative means for holding the handle 6' of the microabrader device together would be to have a solid post protruding through upper portion 6u and a ring or cap friction-fitted over the end of the post to retain the outer portion spring and lower portion together. As the microabrader devices may be disposable, the ring or cap could be fixed permanently via adhesive, for example.

While the user feedback is disclosed and shown as a vertical printed matter gauge, it would be possible to have pressure indication performed in other ways known to those skilled in the art. For example, instead of a vertical printed matter gauge, the printed matter gauge may be disposed horizontally on the reverse side of flat front surface 12' outside of the inner sleeve. This could be achieved by a pressure sensitive film placed on the reverse side of flat front surface 12', which may be a horizontal bar that grows depending on the amount of pressure applied to the abrading surface 5". Another way of performing pressure indication would have the compression of upper portion 6u activate a cam mechanism, which would cause a radial arm to rotate about a center point of a circular printed-matter gauge.

In yet another embodiment according to the invention, a torsional spring instead of a compression spring could be used as spring 6s. With a rotary mechanism and torsional spring, the rotational force is transferred to a downward force. A cam mechanism associated with the torsion spring would cause a pointer to indicate the amount of pressure applied at the printed-matter gauge. Thus, the user or technician would have to apply a threshold level of pressure before the upper portion 6u would collapse over the lower portion 61. The threshold level of pressure would be directly related to the appropriate amount of pressure to be applied to the abrading surface 5". Thus, the technician could have both a tactile and visual indication of the amount of pressure being applied to abrade the skin of a patient. A tactile indication of the amount of pressure could be achieved with a detent as described above. The microabrader with controlled abrasion features envisions all known means to provide a visual or tactile indication of the amount of compression in a known spring. The employment of visual and/or tactile feedback to a user should allow for a more consistent application of the microabrader and thus provide better reproducibility of abrasion and a better rate of drug delivery and vaccine efficacy.

In view of the use of compression to obtain the appropriate pressure with which to abrade a patient's skin, it is envisioned that the microabrader device of FIG. 9 could be modified to have holes in the bottom of flat front surface 12' for the delivery of liquid (e.g., drug or vaccine). Thus, when upper portion 6u of the micoabrader device collapses onto lower portion 61, the liquid would be expressed either by mechanical means or puncturing a bladder containing the liquid and then allowing the pressure and gravity feed the liquid to the surface of the patient's skin. Such a microabrader device would be useful for holding a drug or vaccine to be delivered via the abrasion technique, as well as holding a fluid to be use for reconstitution of a substance on the microabrading surface. With such an embodiment, the microabrader device and drug or vaccine could be in a single package, which is disposable. And after the package is opened, one would simply apply the microabrader device to the patient's skin and after the skin is abraded and the drug or vaccine is delivered, the microabrader device would be disposed of in the usual manner.

While the microprotrusions themselves may preferably be frustoconical in design in order to control the depth of penetration of the abrading surface, a device which houses the abrader chip or the abrading surface may also control the depth. As shown in FIGS. 10A-D, an applicator frame or housing includes a track or "slot" along which an abrader chip is moved. Similar to the housing of the rotary delivery device, the bottom surface 112 of the applicator frame stretches the patient skin and thus adds tension keeping the skin taut while the abrader chip moves across the patient's skin. The track of the applicator frame determines the depth of the penetration of the solid microneedles (microprotrusions) so that a constant depth of penetration is achieved during the back and forth motion of the microabrader device.

Figure 10A:
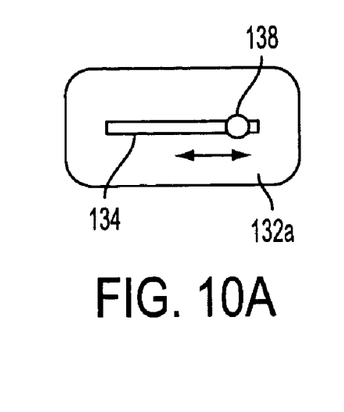
FIGS. 10A-E illustrate manual, lateral abraders with applicator frames according to the invention.
Figure 10B:
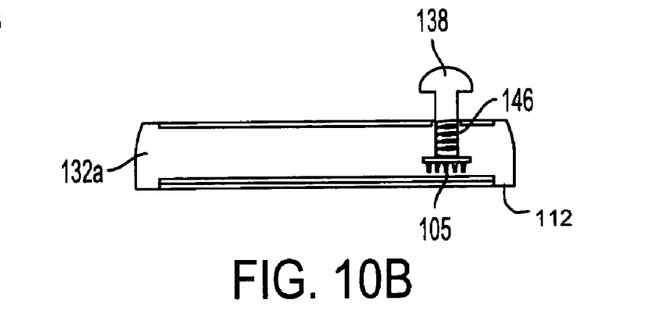
Figure 10C:
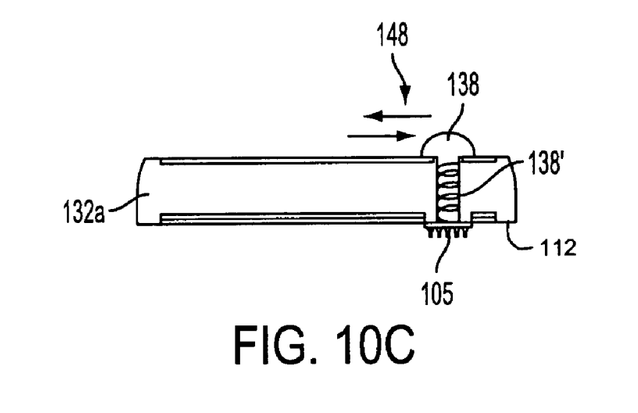

According to the embodiment shown in FIGS. 10A-C, a flat patch-like device 132a that contains a central "slot" 134 with a movable button 138 disposed therein is fixedly attached to a desired delivery site of a patient's skin. Device 132a may be attached with an adhesive or other fixings means known to be safe in attaching objects to skin. Moveable button 138 is connected to a spring-loaded bar 138' that is attached to an abrader chip 105. This simple microabrader device 132a is positioned on a patient's skin through which a vaccine or other drug is desired to be delivered. The spring-loaded bar 138' maintains the abrader chip within flat patch-like device 132a away from the patient's skin, as shown in FIG. 10B. Button 138 is pressed activating a spring 146, which forces chip 105 down toward the skin at a specific force (see side view FIG. 10C). The specific force applied to the skin by the spring-loaded bar 138' is preferable an optimal force to achieve seating of the vaccine or drug into the patient's skin. Once activated, spring 146 exerts a defined and constant pressure on chip 105 to keep it in contact with the skin at this defined pressure.

As illustrated in FIG. 10C, after spring-loaded bar 138' and button 138 cause abrader chip 105 to move into contact with a patient's skin, chip 105 is moved laterally across the patient's skin in the direction of arrows 148. This is achieved by moving activated button 138 laterally along the "slot" 134. The "slot" 134 is an elongated opening in the top of flat patch-like device 132 and defines the abrasion path length. If re-abrasion of the same area is desired, one would simply move button 138 in the opposite direction along the "slot" path. Once the desired number of passes is accomplished, the flat patch-like device can be removed from the patient's skin. In order for safe disposal of the abrader, which has contacted bodily fluids, button 138 may be deactivated to retract chip 105 back within flat patch-like device 132*a*.

Figure 10D:
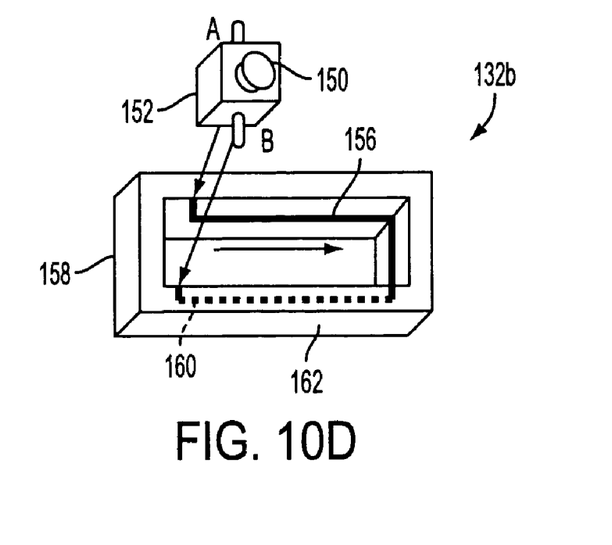

FIG. 10D shows yet another embodiment according to the invention. This device 132*b* includes an applicator head 150 with an abrader chip 152 or off-the-shelf microabrader device. Applicator head 150 has two pins A and B affixed to opposing sides thereof. A track 156 is located on the inner vertical walls of an applicator frame 158 and may be either grooves for receiving pins or a projecting flange cooperating with the sides of the applicator head including an abrader chip or abrading surface. The track 156 of the applicator frame 158 shown in FIG. 10D includes a groove 160 extending from the top of applicator frame 158 to a depth where the track (groove) continues laterally. The height of the lateral track 156 from the bottom of applicator frame 158 adjacent the skin surface remains constant over the lateral distance so that the track determines the depth of penetration of the microprotrusions, which results in furrows with a substantially consistent depth. Two pins A and B are inserted into the grooves 160 at the top of applicator frame 158 so that the abrader chip 152 or abrading surface of a microabrader device follows the track 156 and has a consistent penetration depth while being abraded across the skin's surface.

The bottom surface 162 of the applicator frame 158 may have a narrow outer edge, which aids in providing uniform tensioning of the patient's skin during the abrasion process. The area confined by the applicator frame 158 in which the abrading chip or abrading surface moves along the track remains constant and thus provides a constant skin treatment area and the narrow outer edge of the bottom surface 162 ensures uniform skin tension to facilitate the abrasion process. As shown in FIG. 10D, the abrader chip 152 or abrading surface is attached to the bottom surface of an applicator head or a microabrader device including a handle. The abrasion is achieved by manually or mechanically moving abrader chip 152 or abrading surface within track 156 (in the direction shown in the figure) back and forth while keeping applicator frame 158 firm and stationary on the treatment site.

Figure 10E:
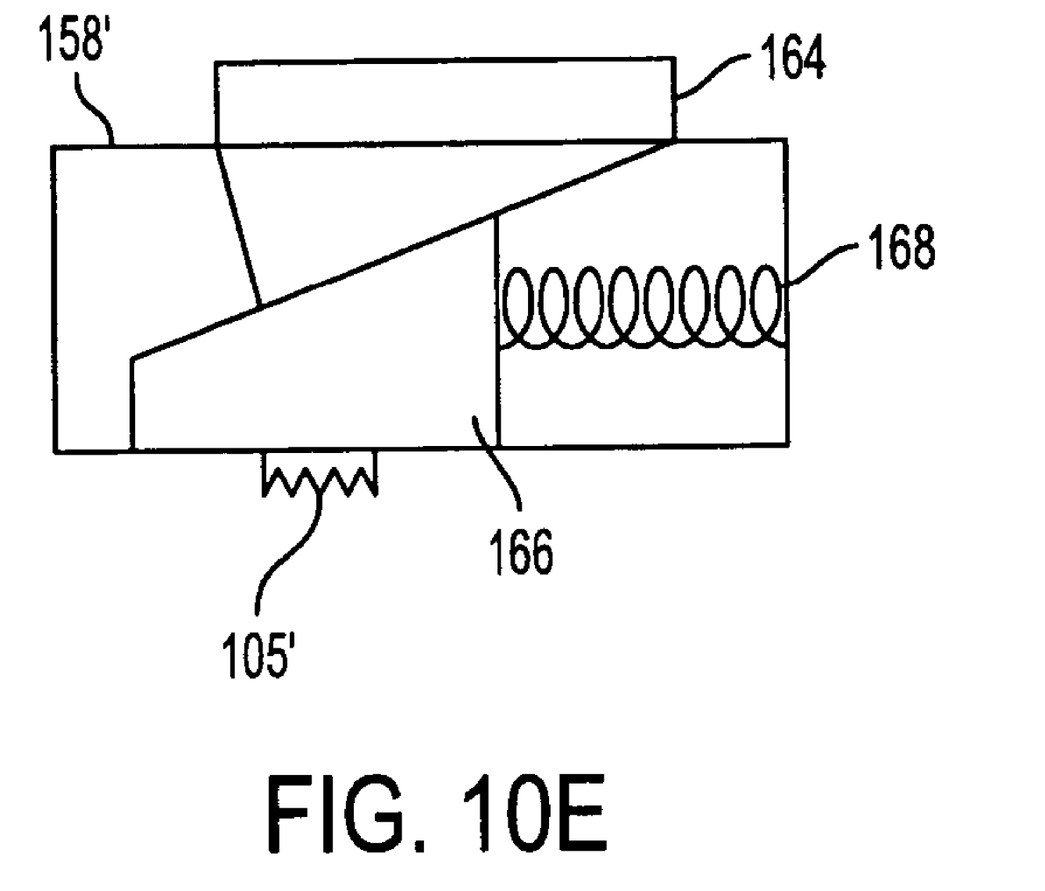

In another embodiment of a flat patch-like device illustrated in FIG. 10E, a driving wedge 164 and a moving wedge 166 are disposed within an applicator frame 158'. The applicator frame 158' is placed on a subject's arm so that an abrader chip 105' mounted on a surface of moving wedge 166 is pressed into the subject's skin as the driving wedge 164 is moved toward spring 168. As an operator presses against driving wedge 164, two forces are produced: an "x" force, which moves the driving wedge across the subject's skin and a "y" force, which presses abrader chip 105' against the subject's skin as the moving wedge is pushed across the subject's skin by driving wedge 105'. When the stroke is finished (driving wedge 164 moves moving wedge 166 against spring 168 and compressing the same) and pressure on driving wedge 164 is released, compressed spring 168 pushes moving wedge 166 and driving wedge back to their original position. That is, spring 168 resets the device for the next abrading stroke. The flat patch-like device according to embodiment 10E would be designed so that the moving wedge applies sufficient downward pressure onto abrader chip 105' so that sufficient abrasion is achieved to ensure delivery of drugs rubbed on the subject's skin that is abraded. The wedges of this device would be designed to control pressure as the abrader chip moves across the subject's skin and controls the area of skin that is abraded. Therefore, the wedge angle and spring force may be varied to control these parameters. The entire patch-like assembly may be disposable, or, only the moving wedge 166 with abrader chip 105' may be disposable. In that instance, the patch-like device would be designed to receive replaceable moving wedges 166.

In addition to providing constant depth of penetration of the solid microneedles (microprotrusions) into the epidermis, uniform skin tension to facilitate the abrasion process and constant skin treatment area, the applicator frame and applicator head embodiment may include spring-loaded applicator heads. That is, the applicator head including the abrader chip or abrading surface may be mounted on springs to provide a constant downward application force, as in the embodiment shown in FIGS. 10A-C. As shown in the Figures, the constant downward force can be applied by a line of coil springs or a molded wave spring disposed between the frame and the abrader surface. Such improvements upgrade the functionality of the drug delivery device by eliminating and/or reducing the operator-to-operator variability.

Figure 11A:
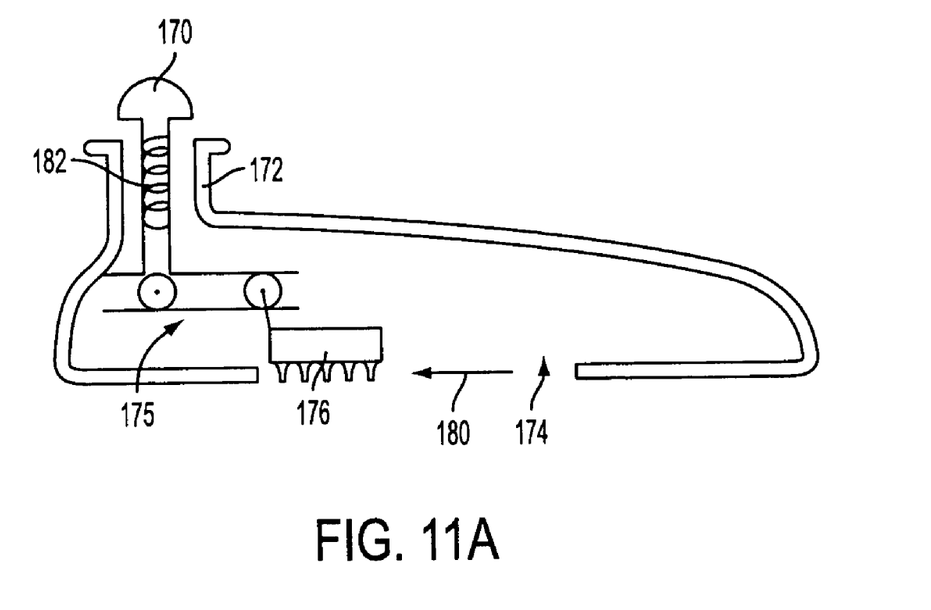
FIGS. 11A and B illustrate an automatic lateral abrader.
Figure 11B:
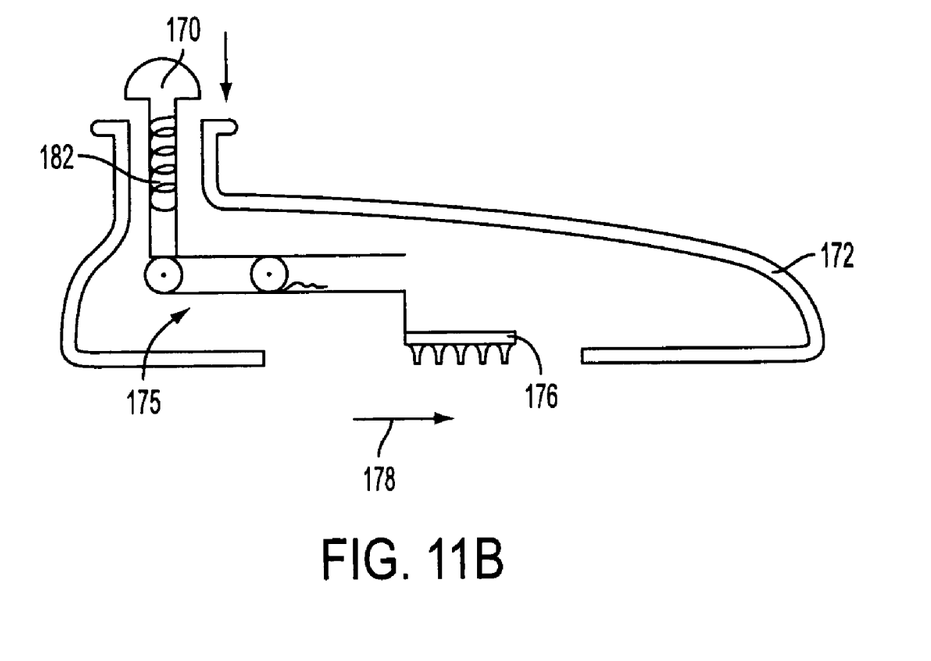

The embodiment schematically illustrated in FIGS. 11A and B employs a user-activated spring-loaded push button 170 disposed adjacent a housing 172 with an opening 174. Inside housing 172, which may be made out of a plastic material, a series of levers or perpendicularly arranged horizontal bars 175 cause the abrader chip 176 to move across opening 174 in the directions shown in the Figures. Housing 172 is fixedly attached to an area a skin where a vaccine or other agent is desired to be delivered. FIG. 11A shows the position of abrader chip 176 when button 170 is in its resting position or deactivated position. In the resting or deactivated position, abrader chip 176 is at one side of the opening 174 of housing 172. When button 170 is pressed or activated, abrader chip 176 moves in one direction (arrow 178) toward the other side of opening 174, as shown in FIG. 11B. When button 170 is released or deactivated, abrader chip 176 moves in the opposite direction (arrow 180—FIG. 11A) back to its point of origin. The spring mechanism 182 controls the speed at which abrader chip 176 moves across a skin surface and has a spring value that optimally abrades the skin to effectively deliver vaccine, drugs or other agents into the skin. By varying the number of times the user presses the button, one can control the number of passes of abrader chip 176 across the skin treatment area. As explained above, each press(activate)/release(deactivate) cycle results in two passes.

In another embodiment of a rotary delivery device shown in FIG. 7C & 7D, two springs may be used to control the pressure applied and retract the abrading surface within the housing. The first spring may be a pre-loaded spring 46 to control the amount of downward force being applied to the abrading surface of the rotary device. Pressing button 38 activates the spring to push the abrading surface down toward the skin at a specific force that is optimal to achieve seating onto the skin. This spring would be tensioned so that no matter what pressure a person uses to press button 38, the same downward force and rotation would result against a subject's skin. That is, once activated, the spring exerts a defined and constant pressure on the abrading surface to keep it in contact with the skin at this defined pressure. Once the abrading surface is in contact with the skin, the depressed button and threaded housing causes the abrading surface to rotate. The pre-tensioned spring could additionally be designed to control the speed at which the abrading surface rotates against the skin and can be set to a tension that is optimal to effectively abrade the skin and deliver the intended substance. The second spring 46' of this embodiment could be a light spring (i.e., not as stiff as the pre-tensioned spring) and would act as a return spring as described above with respect to spring 46. Pressure control and retraction of the abrading surface may be achieved with a single preloaded spring where the spring will deflect only if sufficient pressure necessary to penetrate the stratum corneum is present. The design of the spring or springs are chosen so that the abrading surface will retract within the housing upon release of the push button.

Applicants additionally envision an electronic delivery device. In such a device, a piezoelectric chip, for example, or any kind of electronic device that provides sufficient displacement for abrasion is employed to rotate the microabrader array surface. Such a device would preferably have a spring to determine the amount of downward force applied against a subject's skin in addition to the electronics necessary to rotate the microabrader array surface. In addition, the spring may control the speed of the rotation of the abrading surface and the spring value would be set to optimally effect abrading of the skin.

The preferred method and rotary device would be placed against a subject's skin and then a button would be pressed to force the microabrader array device against the skin in a circular fashion, while a housing of the device remains stationary on the subject's skin. As described above, the movement of the microabrader may be achieved manually, mechanically or electronically and the downward force applied may be controlled by a pre-compressed (pre-loaded) spring, or visually by a technician or electronically via a pressure transducer.

In one preferred method of abrading skin using circular motion, the microabrader device 2 can be rotated across a patient's skin at least two approximate full rotations. That is, the first approximate full rotation could be clockwise, while the second approximate full rotation is counter-clockwise or vice versa. The patient's skin may be abraded in opposite rotational directions. In other embodiments, the microabrader device may be rotated approximately 180° against the skin in either direction. The structural design of microarray of the microabrader device according to the invention enables the vaccine, drug solution or other agent to be absorbed more effectively thereby allowing less of the vaccine, drug solution or other agent to be applied to a patient's skin or to coat abrading surface 5.

Depending upon the vaccine, drug solution or other agent being applied using the microabrader device, differing microprotrusion arrays forming the abrading surface may perform better. It will be understood that the above description of the present invention is described with respect to preferred embodiments employ coil springs in the design of the device, however, coil springs are not the only type of biasing element that may be employed. Leaf springs, compressible foams, and other biasing means known to the art may be employed in the present invention with the same results. It will also be understood that the above description of the present invention is described with respect to preferred embodiments and that the illustrated embodiments are susceptible to various modifications, changes and adaptations, and the same are intended to be comprehended within the meaning and range of equivalents of the appended claims.

We claim:

1. An abrader device for delivering a substance into skin via an abrasion process, said abrader device comprising:

a base having a top surface and a bottom surface onto which an abrader surface with microprotrusions is mounted, said microprotrusions are frustroconical protrusions and each protrusion having at least one scraping edge for forming a furrow along a length of the skin;

a housing surrounding the base;

a handle having a pushbutton projecting from a top surface of the device;

wherein said pushbutton has a first detent, wherein said first detent is engagable with a cooperating detent on said base and said detents cooperate to prevent inadvertent movement of said handle with respect to said base wherein said first detent of said pushbutton and said detent on said base hold the pushbutton in a substantially extended position prior to use wherein the pushbutton collapses inside the base when activated, and the base rotates with respect to the housing and proportionally to the push button collapse, thereby causing the abrader surface to rotate against skin when the housing is placed against skin and a spring operably engaged between the handle and the base, wherein movement of the handle causes proportional compression of the spring for controlling the amount of force or pressure applied to the microprotrusions as the abrader surface moves across the skin thereby forming a furrow of a substantially consistent depth along its length.

2. The abrader device according to claim 1, wherein the microprotrusions are of a depth of about 5 to about 250 microns.

3. The abrader device according to claim 1, wherein said spring is a preloaded spring that deflects only if a sufficient amount of pressure is present, and further comprising a retention detent on said base that engages a portion of said pushbutton after said push button has been fully depressed wherein said retention detent retains said microprotrusions inside said housing after said push button has been fully depressed.

4. The abrader device according to claim 3, wherein said abrader is removably mounted to said base.

5. The abrader device according to claim 1, wherein said abrader is permanently adhered to said base.

6. The abrader device according to claim 1, wherein said abrader is removably mounted to said base.

7. The abrader device according to claim 1, wherein said device further comprises a retraction spring disposed between said housing and said base, wherein said retraction spring retracts the abrader into the device.

8. The abrader device according to claim 1, wherein said device further comprises a first end of said housing which is adapted to stretch the skin when the device is pressed against the skin, thereby providing a tight skin area to aid the abrading surface in scraping the skin area.

9. The abrader device according to claim 7, wherein said housing has a first end adapted to stretch the skin when the device is pressed against the skin, thereby providing a tight skin area to aid the abrader surface in scraping the skin area.

* * * * *